(12) United States Patent
DeLuca et al.

(10) Patent No.: US 8,754,067 B2
(45) Date of Patent: Jun. 17, 2014

(54) 22-HALOACETOXY-HOMOPREGNACALCIFEROL ANALOGS AND THEIR USES

(75) Inventors: Hector F. DeLuca, Deerfield, WI (US); Rafal Barycki, Madison, WI (US); Lori A. Plum, Arena, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 213 days.

(21) Appl. No.: 13/294,524

(22) Filed: Nov. 11, 2011

(65) Prior Publication Data

US 2012/0149669 A1 Jun. 14, 2012

Related U.S. Application Data

(60) Provisional application No. 61/413,225, filed on Nov. 12, 2010.

(51) Int. Cl.
*A61K 31/59* (2006.01)
*C07C 401/00* (2006.01)

(52) U.S. Cl.
USPC ............................................. 514/167; 552/653

(58) Field of Classification Search
USPC ............................................. 552/653; 514/167
See application file for complete search history.

(56) References Cited

U.S. PATENT DOCUMENTS

| | | | |
|---|---|---|---|
| 4,927,815 A | 5/1990 | DeLuca et al. |
| 4,940,700 A | 7/1990 | DeLuca et al. |
| 5,089,641 A | 2/1992 | DeLuca et al. |
| 5,366,731 A | 11/1994 | DeLuca et al. |
| 5,397,776 A | 3/1995 | DeLuca et al. |
| 5,428,029 A | 6/1995 | Doren et al. |
| 5,578,587 A | 11/1996 | DeLuca et al. |
| 5,612,325 A | 3/1997 | Hansen et al. |
| 5,614,512 A | 3/1997 | DeLuca et al. |
| 5,843,928 A | 12/1998 | DeLuca et al. |
| 5,888,994 A | 3/1999 | Hennessy et al. |
| 6,566,352 B1 | 5/2003 | DeLuca et al. |
| 6,579,861 B2 | 6/2003 | DeLuca et al. |
| 6,627,622 B2 | 9/2003 | DeLuca et al. |
| 6,835,723 B2 | 12/2004 | DeLuca et al. |
| 7,101,865 B2 | 9/2006 | Posner et al. |
| 7,718,637 B2 | 5/2010 | DeLuca et al. |
| 7,718,638 B2 | 5/2010 | DeLuca et al. |

OTHER PUBLICATIONS

Deeb et al., "Vitamin D signalling pathways in cancer: Potential for anticancer therapeutics." Nat. Rev. Cancer, vol. 7, pp. 684-700, 2007.*
Jinge Zhu et al, Screening of Selective Inhibitors of 1[alpha],25-Dihyroxyvitamin D3 24-Hydroxylase Using Recombinant Human Enzyme Expressed in *Escherichia coli*, Biochemistry, vol. 49, No. 49, pp. 10403-10411, Nov. 2010.
International Search Report and Written Opinion, PCT International Application No. PCT/US2011/060351, mailed Mar. 21, 2012.

\* cited by examiner

*Primary Examiner* — Barbara P Badio
(74) *Attorney, Agent, or Firm* — Andrus Intellectual Property Law, LLP

(57) ABSTRACT

This invention discloses 22-haloacetoxy-homopregnacalciferol analogs and specifically 22-bromoacetoxy-homopregnacalciferol and pharmaceutical uses therefor. This compound exhibits relatively little calcemic activity and does not promote cellular differentiation off HL-60 leukemia cells, but rather kills the cells. This cell death activity is found in small cell lung carcinoma also, but not in prostate cancer cells. This compound thus causes specific cell death in the absence of changes in calcium levels and without general toxicity in an animal. Therefore it might serve as a useful therapy for treatment of some forms of cancer, such as leukemia and lung cancer.

42 Claims, 9 Drawing Sheets

22-HALOACETOXY-HOMOPREGNACALCIFEROL ANALOGS AND THEIR USES

CROSS REFERENCE TO RELATED APPLICATIONS

This application claims the benefit of U.S. Provisional Application No. 61/413,225, filed Nov. 12, 2010, which is incorporated by reference herein in its entirety for any purpose.

BACKGROUND OF THE INVENTION

This invention relates to vitamin D compounds, and more particularly to 22-haloacetoxy-homopregnacalciferol analogs and their pharmaceutical uses, and especially 22-bromoacetoxy-homopregnacalciferol, its biological activities, and its pharmaceutical uses.

The natural hormone, 1α,25-dihydroxyvitamin $D_3$ and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

A class of secosterol compounds has also been prepared which exhibit high differentiation activity towards malignant cells, such as leukemia cells, but have significantly less of the undesired side-effects (potent calcemic action) of some of the known compounds mentioned above. This selectivity and specificity of action makes the secosterols potentially useful as agents for the treatment of malignancies such as leukemia.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

19-nor vitamin D analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward 22-haloacetoxy-homopregnacalciferol analogs, and their pharmaceutical uses, and more specifically toward 22-bromoacetoxy-homopregnacalciferol, its biological activity, and various pharmaceutical uses for this compound.

Structurally these 22-haloacetoxy-vitamin D analogs are characterized by the general formula I shown below:

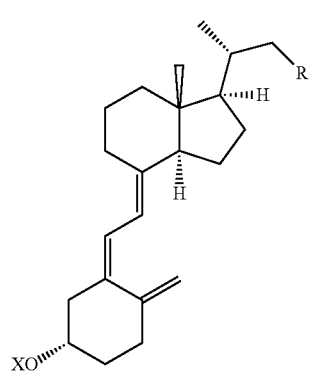

where X is selected from the group consisting of hydrogen and a hydroxy-protecting group, and where the group R represents a haloacetoxy group wherein halo refers to fluoro, chloro, bromo and iodo. Thus, R may be a fluoroacetoxy group ($FCH_2COO-$), a chloroacetoxy group ($ClCH_2COO-$), a bromoacetoxy group ($BRCH_2COO-$), or an iodoacetoxy group ($ICH_2COO-$).

Specific important examples of side chains are the structures represented by formulas (a), (b), (c), and (d) below:

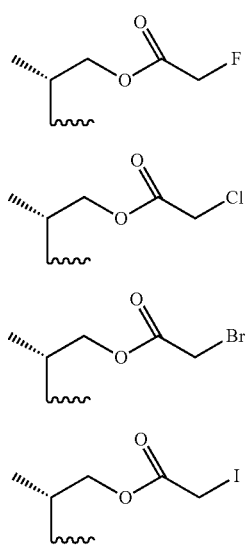

(a)
(b)
(c)
(d)

The preferred analog is 22-bromoacetoxy-homopregnacalciferol (referred to hereinafter as "AB-47") which has the following formula Ia:

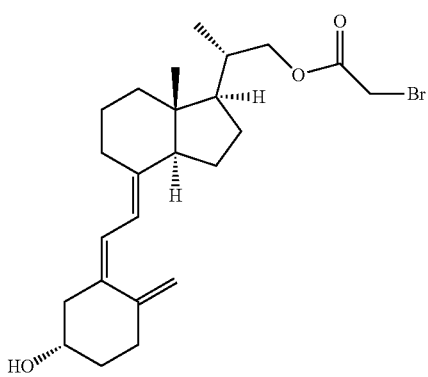

Ia

The above compounds of formula I, especially AB-47, exhibit a desired, and highly advantageous, pattern of biological activity. With regard to calcium regulation, the compound AB-47 exhibits relatively low activity in its ability to mobilize calcium from bone, and in its ability to promote intestinal calcium transport, as compared to the native hormone 1α,25-dihydroxyvitamin $D_3$. Hence, the compound AB-47 can be characterized as having relatively little calcemic activity.

Further, the vitamin D derivative AB-47 does bind the nuclear receptor but with much lower potency (about 100 times less) than the native hormone. Likewise, the potency of AB-47 to stimulate vitamin D receptor mediated gene transcription is extremely low. Interestingly, AB-47 does not promote cellular differentiation of HL-60 cells (leukemia cell line), but rather kills the cells. This cell death activity is found in small cell lung carcinoma also, but not in prostate cancer cells. AB-47 causes specific cell death in the absence of changes in calcium levels and without general toxicity in an intact animal. Thus, the compound AB-47 has potential as an anti-cancer agent and may provide a therapeutic agent for the treatment of leukemia and lung cancer.

One or more of the compounds may be present in a composition to treat the above-noted diseases in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually, or parenterally in dosages of from about 0.01 μg/day to about 1000 μg/day, preferably from about 0.1 μg/day to about 500 μg/day.

BRIEF DESCRIPTION OF THE DRAWINGS

FIGS. 1-9 illustrate various biological activities of 22-bromoacetoxy-homopregnacalciferol, referred to herein as "AB-47," as compared to the native hormone 1α,25-dihydroxyvitamin $D_3$, hereinafter "1,25$(OH)_2D_3$,"

FIG. 1 is a graph illustrating the relative activity of AB-47 and 1,25$(OH)_2D_3$ to compete for binding with [$^3$H]-1,25-$(OH)_2$-$D_3$ to the full-length recombinant rat vitamin D receptor;

FIG. 2 is a graph illustrating the percent HL-60 cell differentiation as a function of the concentration of AB-47 and 1,25$(OH)_2D_3$;

FIG. 3 is a graph illustrating the in vitro transcription activity of 1,25$(OH)_2D_3$ as compared to AB-47;

FIG. 7 is a bar graph illustrating the bone calcium mobilization activity of 1,25$(OH)_2D_3$ as compared to AB-47;

FIG. 8 is a bar graph illustrating the intestinal calcium transport activity of 1,25$(OH)_2D_3$ as compared to AB-47; and FIG. 9 is a bar graph illustrating change in body weight of animals given 1,25$(OH)_2D_3$ as compared to AB-47.

DETAILED DESCRIPTION OF THE INVENTION

Figure 1:
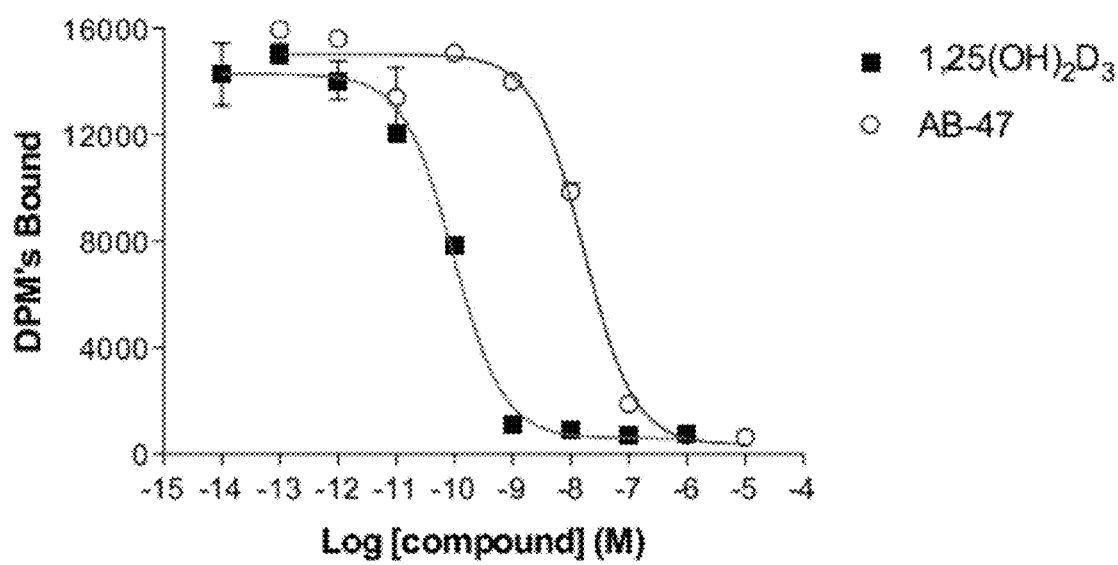

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

The preparation of 22-haloacetoxy-homopregnacalciferol analogs of the basic structure I and particularly 22-bromoacetoxy-homopregnacalciferol (AB-47) of structure Ia, can be accomplished by a common general method, i.e., the condensation of a bicyclic Windaus-Grundmann type ketone II with the allylic phosphine oxide III:

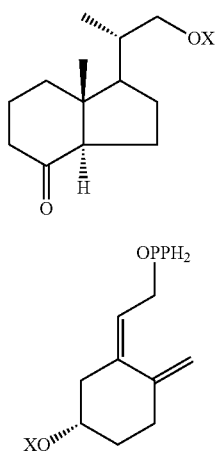

In the structures II and III, group X represents a hydroxy-protecting group as defined above; X being preferably an acyl hydroxy-protecting group in Structure II and t-butyldimethylsilyl (TBS) hydroxy-protecting group in structure III. It should also be understood that any functionalities that might be sensitive, or that interfere with the condensation reaction, be suitably protected as is well-known in the art. The process shown above represents an application of the convergent synthesis concept, which has been applied effectively for the preparation of vitamin I) compounds [e.g. Lythgoe et al., J. Chem. Soc. Perkin Trans. 1, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713)].

Ketones of the general structure II and phosphine oxides of general structure III are known, or can be prepared by known methods.

More specifically, reference should be made to the following illustrative example and description as well as to Scheme 1 herein for a detailed illustration of the preparation of compound AB-47.

In this example specific products identified by Arabic numerals (1, 2, 3, etc.) refer to the specific structures so identified in the Scheme 1.

EXAMPLE

Chemistry. Melting points (uncorrected) were determined on a Thomas-Hoover capillary melting-point apparatus. Optical rotations were measured in chloroform using a Perkin-Elmer 241 automatic polarimeter at 22° C. Ultraviolet (UV) absorption spectra were recorded with a Perkin-Elmer Lambda 313 UV-VIS spectrophotometer in ethanol. $^1$H nuclear magnetic resonance (NMR) spectra were recorded in deuteriochloroform at 400 and 500 MHz with Bruker DMX-400 and Bruker DMX-500 spectrometers, respectively. $^{13}$C nuclear magnetic resonance (NMR) spectra were recorded at 100 and 125 MHz with the same spectrometers in deuteriochloroform. Chemical shifts (δ) were reported downfield from internal Me$_4$Si (δ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example 1

Preparation of
22-bromoacetoxy-homopregnacalciferol (5,AB-47)

1 was prepared according to standard procedures from Vitamin D$_2$.

The structure of 4 has been mentioned by Kutner et al. (*Tetrahedron Letters*. Vol. 28, No. 49, pp. 6129-6132, 1987)

22-Hydroxy-homopregnacalciferol (4). To a stirred solution of 2 in THF (2 ml) 2 drops of 1.8M solution of PhLi in (n-Bu)$_2$O was added at −25° C. until deep orange color persisted. Then stoichiometric amount (100 μl; 180 μmol) of PhLi solution was added. After 30 min. the mixture was cooled to −78° C. and a solution of 1 in THF (1 ml) was siphoned via cannula. After 2 h cooling bath was removed and the mixture was stirred for next 2 h at 0° C. Saturated aqueous solution of NH$_4$Cl (1 ml), brine (2 ml) and water (1 ml) was added and the mixture was extracted with CH$_2$Cl$_2$ (3×15 ml). Organic phase was dried over anhydrous Na$_2$SO$_4$ and concentrated under reduced pressure. The residue was purified on Waters silica gel Sep-Pack cartridge (0-10% AcOEt/hexane) to give 74 mg (152 μmol; 91% yield) of 3.

3 was dissolved in MeOH (2 ml) and treated with CSA (50 mg; 216 μmol) for 3 h. Saturated aqueous solution of NaHCO$_3$ (1 ml), brine (2 ml) and water (1 ml) was added and the mixture was extracted with CH$_2$Cl$_2$ (3×15 ml). Organic phase was dried over anhydrous Na$_2$SO$_4$ and concentrated under reduced pressure. The residue was purified on Waters silica gel Sep-Pack cartridge (20-50% AcOEt/hexane) to give 33 mg (100 μmol; 66% yield) of 4. $^1$H NMR (400 MHz, CDCl$_3$) ☐ 0.57 (3H, s), 1.05 (3H, d, J=6.6 Hz), 2.14-2.21 (1H, m), 2.28 (1H, dd, J=13.0 Hz, J=7.6 Hz), 2.37-2.43 (1H, m), 2.57 (1H, dd, J=13.0 Hz, J=3.0 Hz), 2.81-2.85 (1H, m), 3.38 (1H, dd, J=10.4 Hz, J=6.9 Hz), 3.65 (1H, dd, J=10.4 Hz, J=2.8 Hz), 3.94 (1H, m), 4.82 (1H, d, J=1.5 Hz), 5.05 (1H, s), 6.04 (1H, d, J=11.2 Hz), 6.23 (1H, d, J=11.2 Hz); $^{13}$C NMR (101 MHz, CDCl$_3$) ☐ 12.0, 16.9, 22.3, 23.5, 27.2, 29.0, 31.9, 35.1, 39.1, 40.3, 45.8, 45.9, 52.8, 56.0, 67.9, 69.2, 112.4, 117.6, 122.3, 135.3, 141.9, 145.1; MS (EI) m/z 330 (M$^+$, 44), 297

(18), 271 (11), 136 (95), 118 (100); exact mass calculated for $C_{22}H_{34}O_2$ 330.2554, measured 330.2557.

22-Bromoacetoxy-homopregnacalciferol (5). To a vigorously stirred solution of 4 (33 mg; 100 μmol) and DMAP (2 crystals) a solution of DCC (52 mg; 252 μmol) in $CH_2Cl_2$ (250 μl) and a solution of bromoacetic acid (17 mg; 120 μmol) in $CH_2Cl_2$ (120 μl) was added dropwise at 0° C. Cooling bath removed and the mixture was stirred for 30 min. The mixture was purified on Waters silica gel Sep-Pack cartridge (10-30% AcOEt/hexane) and subsequently on HPLC (5% i-PrOH/hexane; Zorbax Rx-Sil 9.4×250 mm, 5 μm; 4 ml/min.; $R_t$=5.43 min.) to give 19 mg (42 μmol; 42% yield) of 5. UV (EtOH) $\lambda_{max}$=264 nm; $^1$H NMR (500 MHz, $CDCl_3$) δ 0.57 (3H, s), 1.05 (3H, d, J=6.6 Hz), 2.15-2.20 (1H, m), 2.29 (1H, dd, J=13.0 Hz, J=7.6 Hz), 2.38-2.43 (1H, m), 2.57 (1H, dd, J=13.0 Hz, J=2.5 Hz), 2.82-2.85 (1H, m), 3.86 (2H, s), 3.90-3.95 (2H, m), 4.19 (1H, dd, J=10.7 Hz, J=3.2 Hz), 4.81 (1H, d, J=1.2 Hz), 5.05 (1H, s), 6.04 (1H, d, J=11.2 Hz), 6.23 (1H, d, J=11.2 Hz); $^{13}$C NMR (126 MHz, $CDCl_3$) δ 12.0, 17.2, 22.3, 23.4, 25.9, 27.1, 28.9, 31.9, 35.1, 36.2, 40.3, 45.9, 52.9, 55.9, 69.2, 71.2, 112.5, 117.8, 122.2, 135.5, 141.5, 145.0, 167.4; MS (EI) m/z 452 ($M^+$, 9), 450 ($M^+$, 10), 419 (5), 355 (9), 136 (100); exact mass calculated for $C_{24}H_{35}BrO_3$ 450.1765, measured 450.1763.

SCHEME 1 is set forth below.

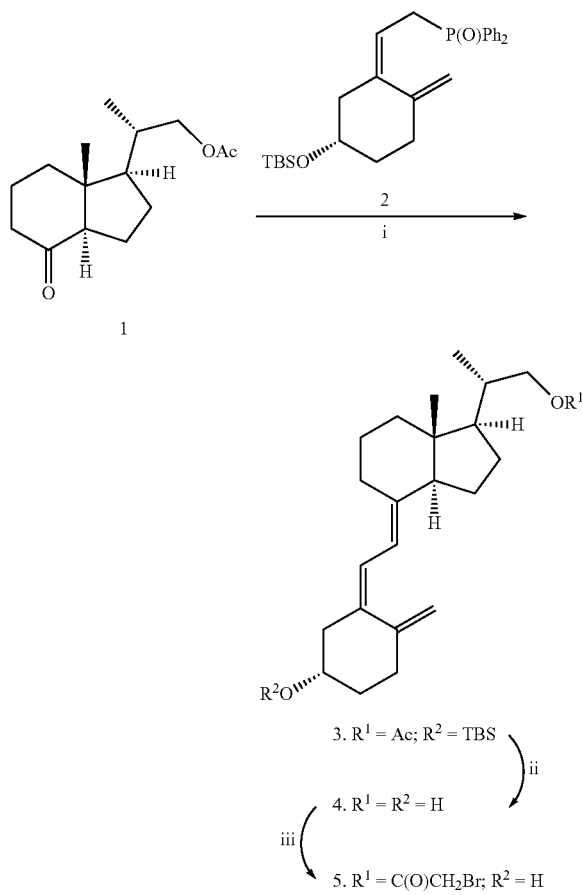

(i) 2, PhLi, THF, 91%;
(ii) CSA, MeOH 66%;
(iii) bromoacetic acid, DCC, DMAP, $CH_2Cl_2$, 42%.

Biological Activity of
22-Bromoacetoxy-Homopregnacalciferol (AB-47)

As illustrated in FIG. 1, the compound AB-47 competes for binding to the nuclear vitamin D receptor with 100 times less potency than 1,25-$(OH)_2D_3$ (FIG. 1). It might be expected from these results that compound AB-47 would not have any desirable biological activity. Surprisingly, however, compound AB-47 is a highly selective analog with unique biological activity.

Figure 8:
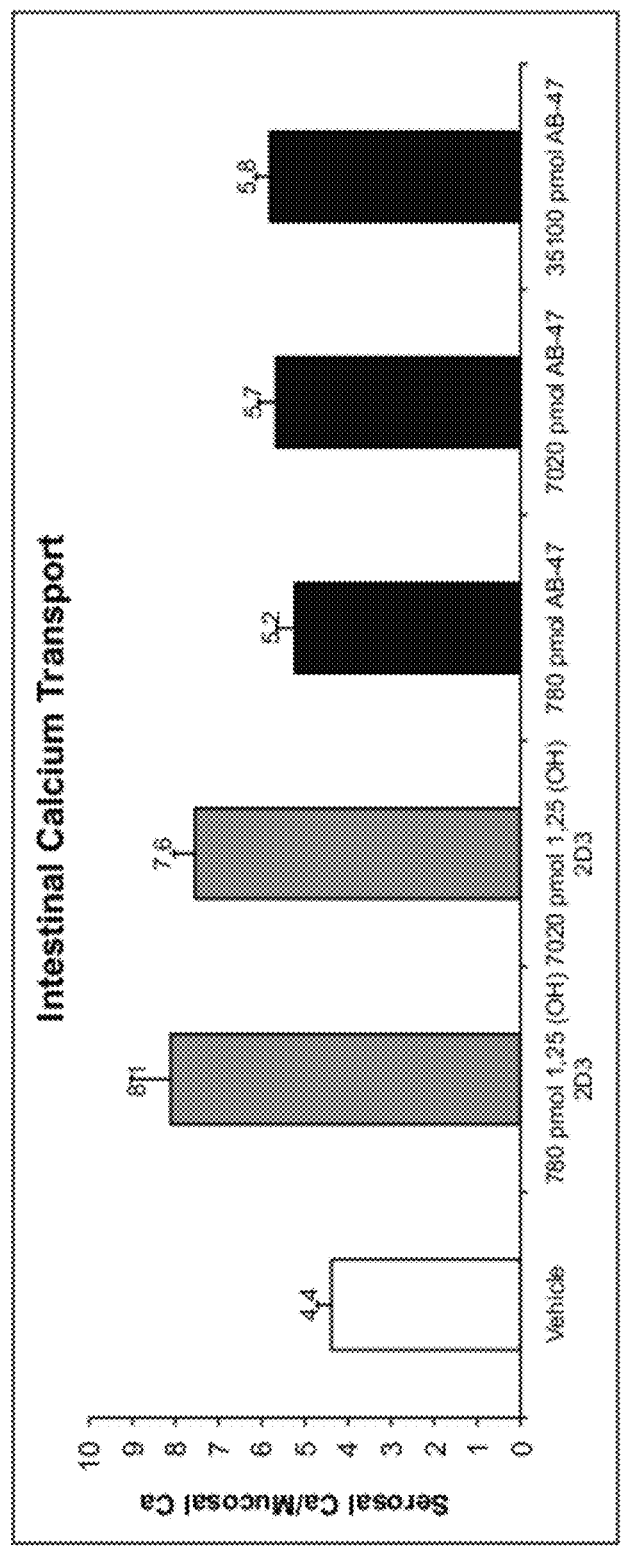

FIG. 8 shows that AB-47 has relatively low activity as compared to that of 1,25-dihydroxyvitamin $D_3$ (1,25$(OH)_2$ $D_3$), the natural hormone, in stimulating intestinal calcium transport. AB-47 does not promote intestinal calcium transport to any significant degree even at the highest dose tested (35,100 pmol).

Figure 7:
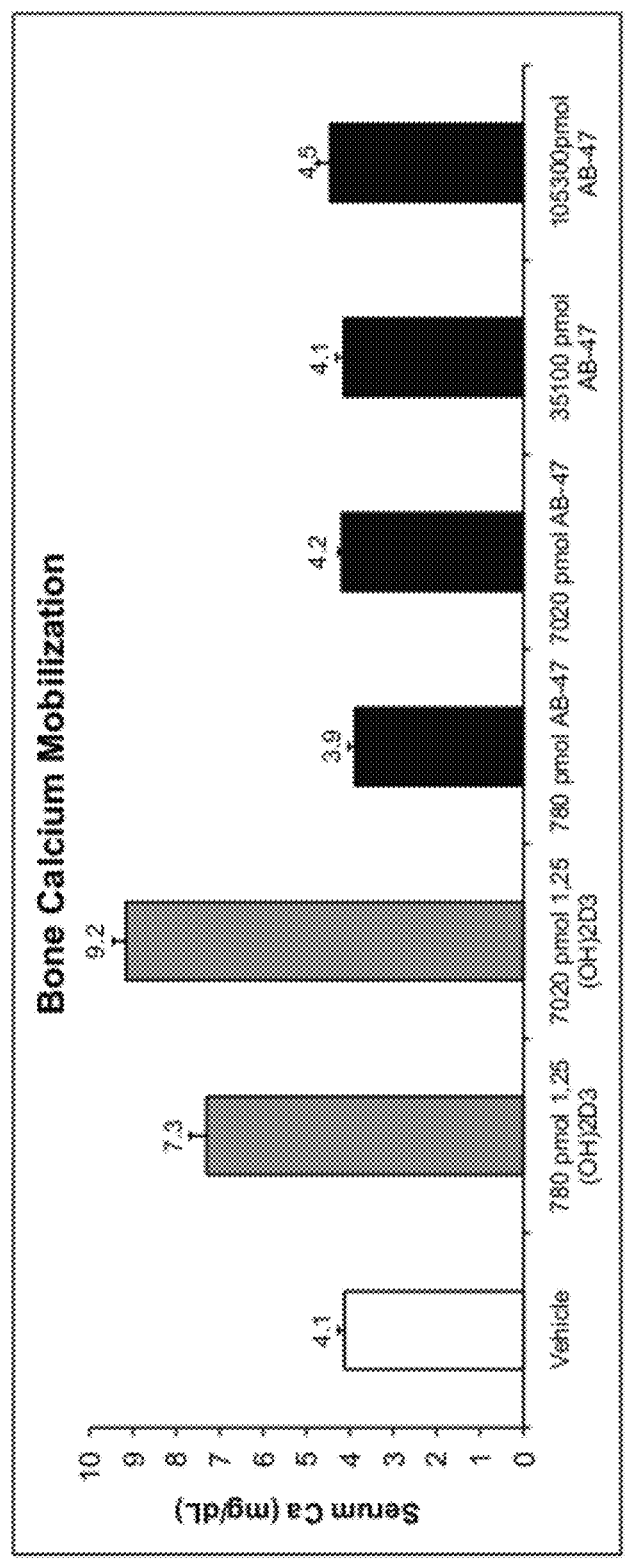

FIG. 7 demonstrates that AB-47 has relatively low bone calcium mobilization activity, as compared to 1,25$(OH)_2D_3$. AB-47 is less potent than the native hormone in releasing bone calcium stores as little to no activity is observed even at the highest dose administered (105,300 pmol); whereas, significant increases in serum calcium are observed at 780 pmol when the native hormone is given.

FIGS. 7 and 8 thus illustrate that AB-47 may be characterized as having relatively low calcemic activity.

Figure 2:
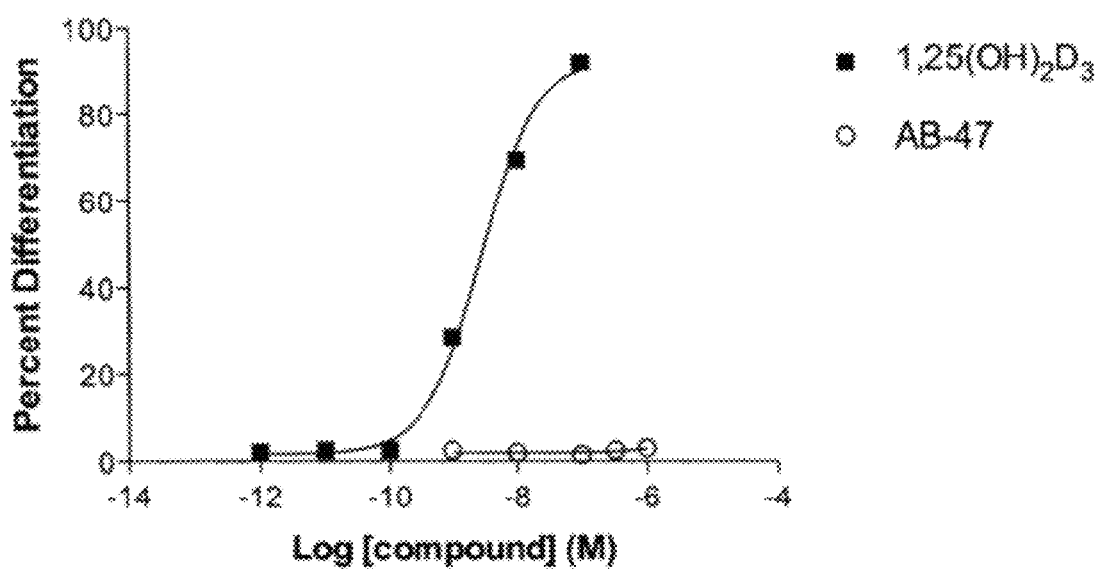

FIG. 2 illustrates that AB-47 does not promote differentiation in HL-60 leukemia cells.

Figure 3:
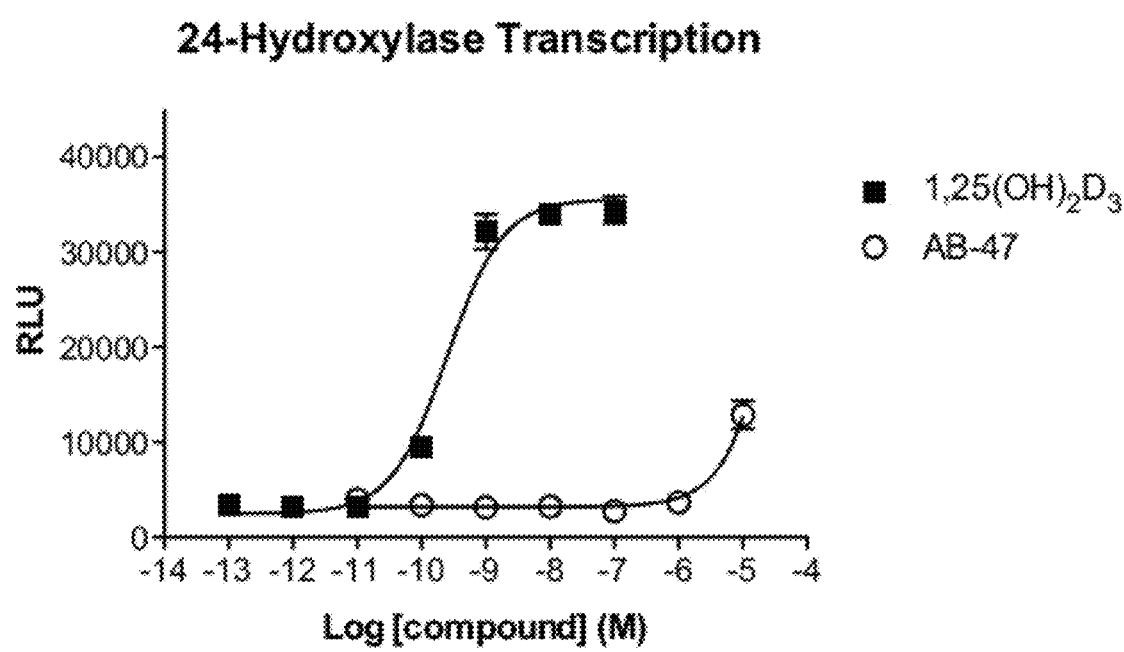

FIG. 3 illustrates that the compound AB-47 lacks activity in increasing transcription of the 25-hydroxylase gene in bone cells until very high doses are administered.

Figure 4A:
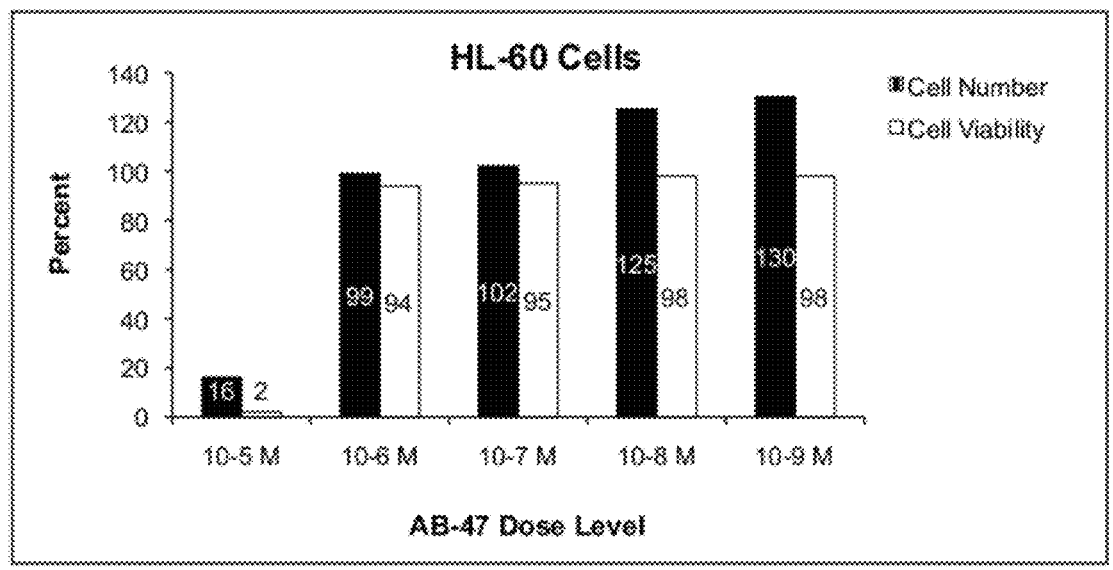
FIG. 4A is a bar graph illustrating cell viability of HL-60 leukemia cells as a function of the dose level of AB-47.
Figure 4B:
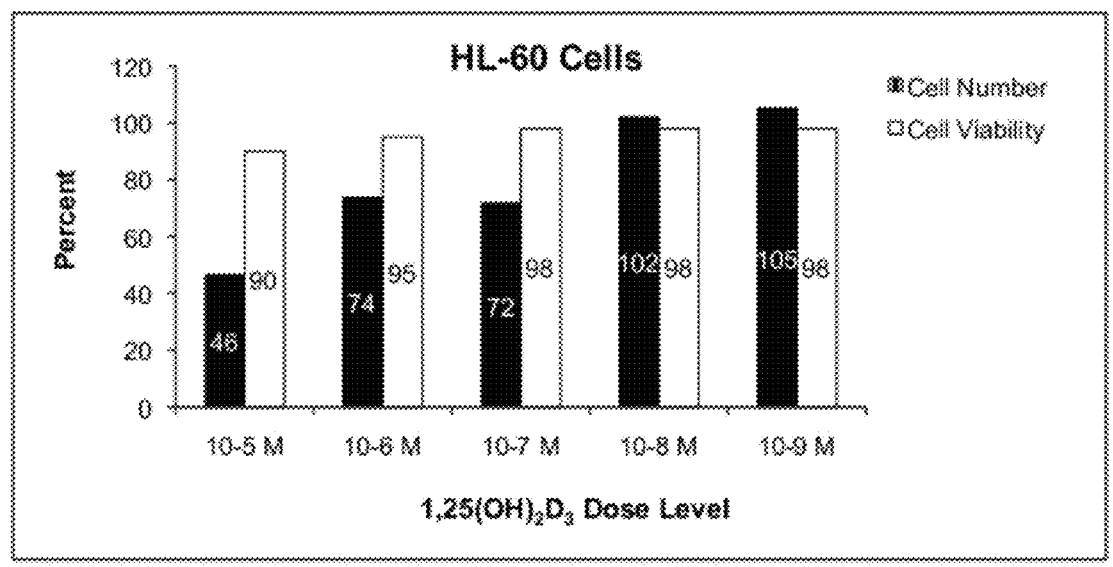
FIG. 4B is a bar graph illustrating cell viability of HL-60 leukemia cells as a function of the dose level of 1,25$(OH)_2D_3$.

FIG. 4A illustrates that AB-47 kills HL-60 leukemia cells. In contrast, FIG. 4B illustrates that 1,25$(OH)_2D_3$ does not have any significant effect on the viability of HL-60 leukemia cells.

Figure 5A:
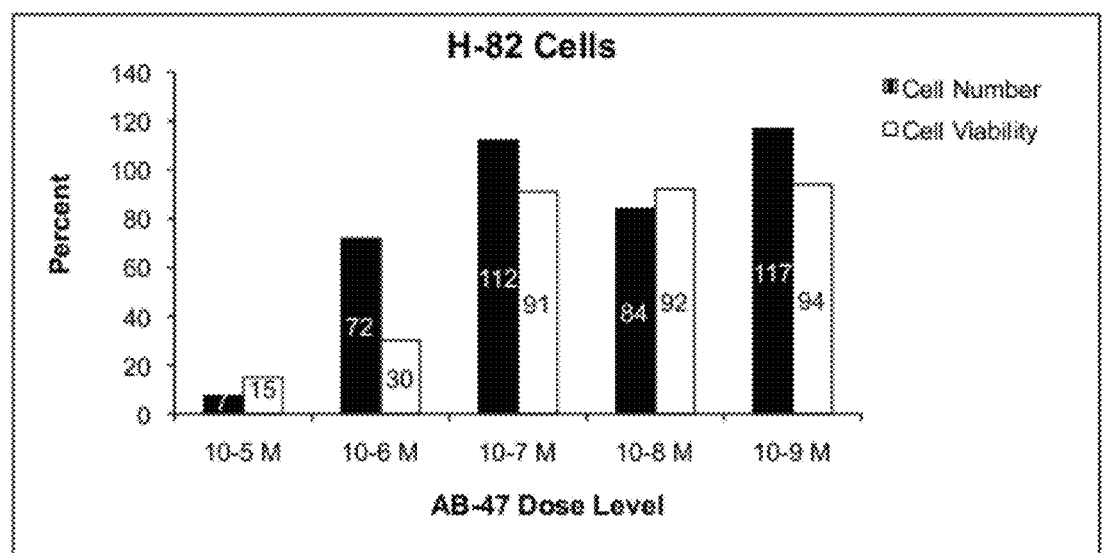
FIG. 5A is a bar graph illustrating cell viability of H-82 lung carcinoma cells as a function of the dose level of AB-47.
Figure 5B:
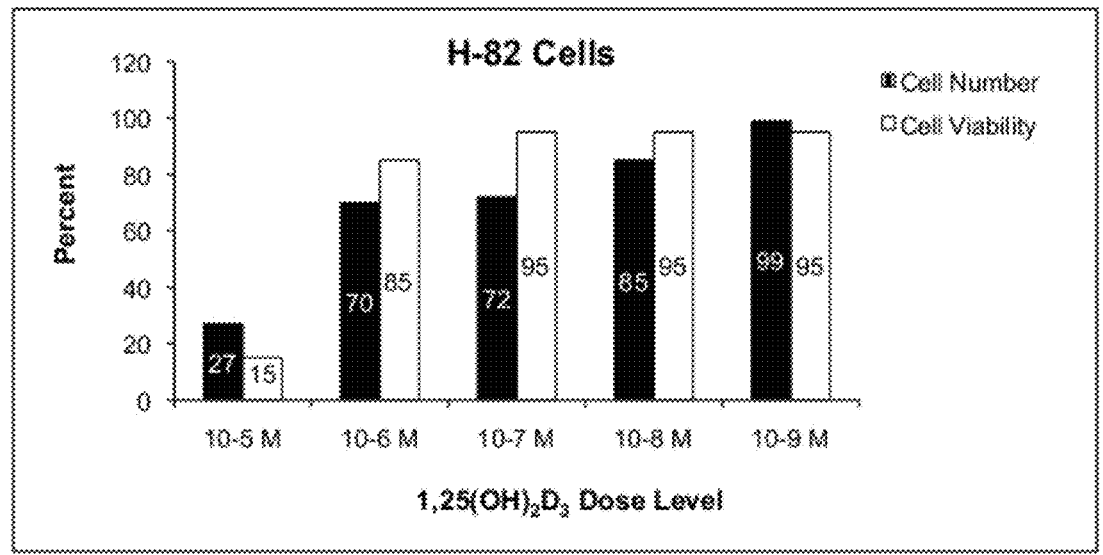
FIG. 5B is a bar graph illustrating cell viability of H-82 lung carcinoma cells as a function of the dose level of 1,25$(OH)_2D_3$.

FIG. 5A illustrates that AB-47 kills H-82 lung carcinoma cells. In contrast FIG. 5B illustrates that 1,25$(OH)_2D_3$ does not have any significant effect on the viability of H-82 lung carcinoma cells.

Figure 6A:
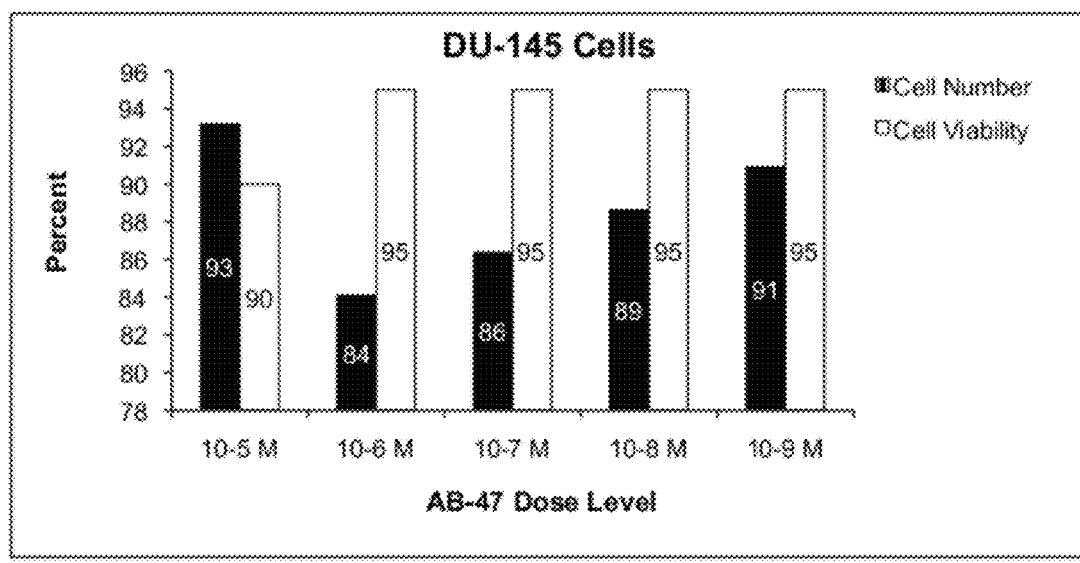
FIG. 6A is a bar graph illustrating cell viability of DU-145 prostate cells as a function of the dose level of AB-47.
Figure 6B:
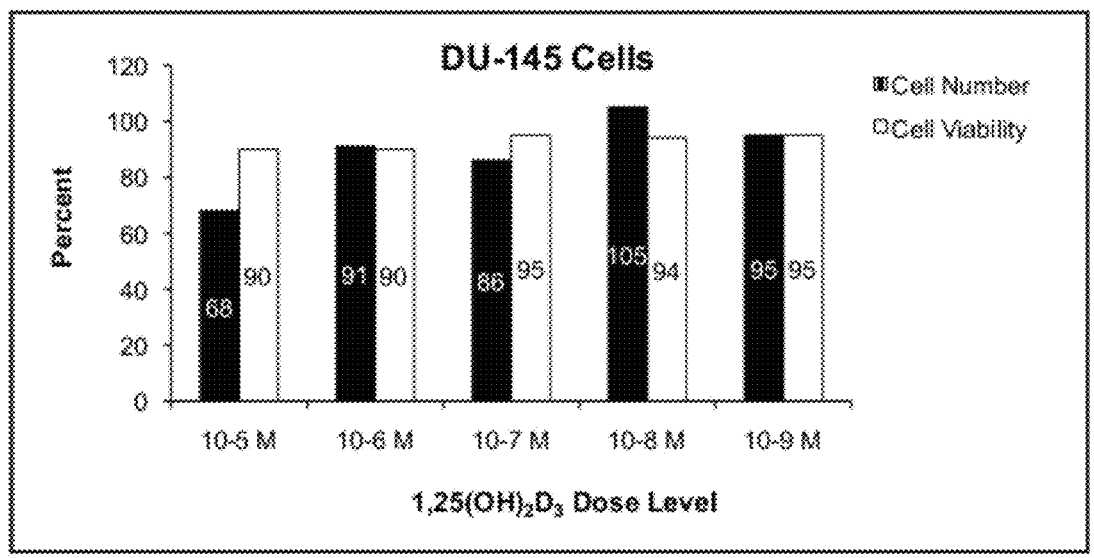
FIG. 6B is a bar graph illustrating cell viability of DU-145 prostate cells as a function of the dose level of 1,25$(OH)_2D_3$.

FIGS. 6A and 6B illustrate that neither AB-47 nor 1,25 $(OH)_2D_3$ have any significant effect on the viability of DU-145 prostate cells.

Experimental Methods

The compounds of the invention were prepared and studied using the following methods.

Vitamin D Receptor Binding

Test Material
Protein Source
Full-length recombinant rat receptor was expressed in *E. coli BL*21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapatite was collected by centrifugation and then washed three times with Tris-EDTA buffer (50 mM Tris, 1.5 mM EDTA, pH7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24 Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (Suda et al, J. Nutr. 100:1049, 1970) (0.47% Ca)+AEK oil for one week followed by Diet 11 (0.02% Ca)+AEK oil for 3 weeks. The rats were then switched to the same diet containing 0.47% Ca for one week followed by two weeks on the same diet containing 0.02% Ca. Dose administration began during the last week on 0.02% calcium diet. Four consecutive intraperitoneal (ip) doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Cell Growth Experiments

Various cell lines were plated, administered a range of drug concentrations one time, allowed to grow for four days and then the number of cells present counted and expressed as a percentage of those present in the vehicle control plates. Cell viability was assessed by mixing the cells with methylene blue and counting the number of cells that took up the dye (dead cells) and those that did not (live cells). The number of live cells was expressed as a percentage of the total present. Each assay was done in duplicate.

Interpretation of Data

VDR Binding, HL60 Cell Differentiation, and Transcription Activity.

AB-47 ($K_i$=3×10$^{-9}$M) is 100 times less active than the natural hormone 1α,25-dihydroxyvitamin D$_3$ ($K_i$=5×10$^{-11}$M) in its ability to compete with [$^3$H]-1,25(OH)$_2$D$_3$ for binding to the full-length recombinant rat vitamin D receptor (FIG. 1). AB-47 does not promote HL60 differentiation whereas 1α,25-dihydroxyvitamin D$_3$ (EC$_{50}$=2×10$^{-9}$M) has significant HL-60 cell differentiation activity (See FIG. 2). Also, compound AB-47 (EC$_{50}$=>10$^{-6}$M) lacks any transcriptional activity in bone cells unlike 1α,25-dihydroxyvitamin D$_3$ (EC$_{50}$=2×10$^{-10}$ M) (See FIG. 3).

Calcium Mobilization from Bone and Intestinal Calcium Absorption in Vitamin D-Deficient Animals.

Using vitamin D-deficient rats on a low calcium diet (0.02%), the activities of AB-47 and 1,25(OH)$_2$D$_3$ in intestine and bone were tested. As expected, the native hormone (1,25 (OH)$_2$D$_3$) increased serum calcium levels at the dosages tested (FIG. 7). FIG. 7 also shows that AB-47 has little if any activity in mobilizing calcium from bone. Administration of AB-47 at 105,300 pmol/day for 4 consecutive days resulted in little or no mobilization of bone calcium. Thus, it may be concluded that AB-47 does not stimulate the release of bone calcium stores as little to no activity is observed even when 105,300 pmol/rat is administered; whereas, significant increases in serum calcium are observed at 780 pmol when the native hormone is given.

Intestinal calcium transport was evaluated in the same groups of animals using the everted gut-sac method (FIG. 8). These results show that the compound AB-47 is significantly less potent in promoting intestinal calcium transport activity, as compared to 1,25(OH)$_2$D$_3$. AB-47 does not promote intestinal calcium transport as little to no activity is observed even when 35,100 pmol/rat is administered whereas significant increase in activity are observed at 780 pmol when 1,25(OH)$_2$D$_3$ is given. Thus, it may be concluded that AB-47 has low intestinal calcium transport activity at the tested doses.

Body Weight.

Figure 9:
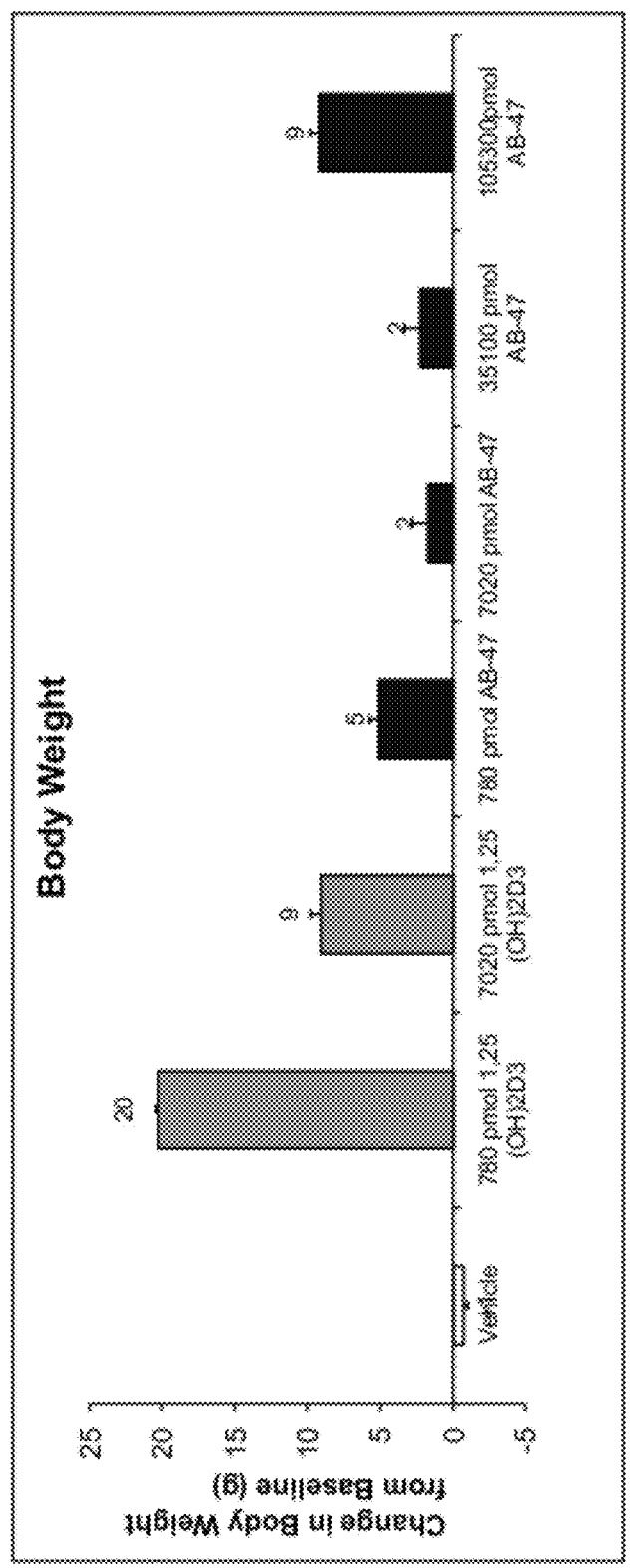

FIG. 9 illustrates that animals given various doses of AB-47 substantially maintain their body weight throughout the test period. The lack of body weight loss suggests there are no other general toxicities observed at these dose levels of AB-47.

Cancer Cell Viability.

FIGS. 4A, 5A and 6A illustrate that AB-47 kills both HL-60 leukemia cells (FIG. 4A) and H-82 lung carcinoma cells (FIG. 5A), but not DU-145 prostate cells. In contrast, FIGS. 4B, 5B and 6B demonstrate that $1,25(OH)_2D_3$ does not significantly effect the viability of any of those three cancer cells.

Summary of the Biological Findings.

The vitamin D derivative AB-47 does bind the nuclear receptor but with much lower potency (about 100 times less active) than the native hormone. Likewise, the potency of this compound to stimulate vitamin D receptor mediated gene transcription is extremely low. Interestingly, AB-47 does not promote cellular differentiation of HL-60 cells (leukemia cell line), but rather kills the cells. This cell death activity is found in small cell lung carcinoma also, but not in prostate cancer cells. AB-47 causes specific cell death in the absence of changes in calcium levels and without general toxicity in an intact animal. Therefore it might serve as a useful therapy for treatment of some forms of cancer, such as leukemia and lung cancer.

These results further demonstrate that AB-47 is an excellent candidate for numerous human therapies, as described herein, and is especially an excellent candidate for treating a cancer because: (1) it causes cell death in HL-60 leukemia cells and H-82 lung carcinoma cells; (2) it has low risk of hypercalcemic liability unlike $1,25(OH)_2D_3$; and (3) it is easily synthesized.

For prevention and/or treatment purposes, the compounds of this invention defined by formula I and Ia may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly AB-47 of formula Ia, may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds 1, particularly AB-47, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds 1, particularly AB-47, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually or parenterally in dosages of from about 0.01 µg/day to about 1000 µg/day, and preferably from about 0.1 µg/day to about 500 µg/day.

The compounds 1, particularly AB-47, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds 1, particularly AB-47, may be advantageously administered in amounts sufficient to provide the desired effect. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound of the structure:

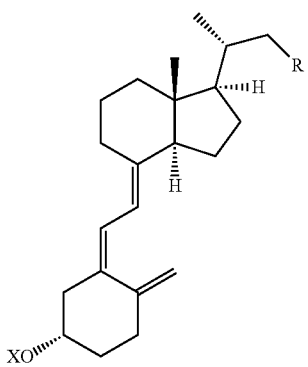

wherein X is selected from the group consisting of hydrogen and a hydroxy-protecting group, and wherein R is selected from a group consisting of fluoroacetoxy, chloroacetoxy, bromoacetoxy or iodoacetoxy.

2. The compound of claim 1 wherein X is hydrogen.

3. The compound of claim 1 wherein R is a fluoroacetoxy group of the formula FCH$_2$C00- and of the structure:

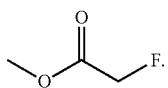

4. The compound of claim 1 wherein R is a chloroacetoxy group of the formula ClCH$_2$C00- and of the structure:

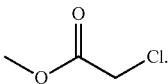

5. The compound of claim 1 wherein R is a bromoacetoxy group of the formula BrCH$_2$C00- and of the structure:

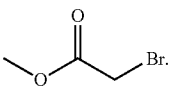

6. The compound of claim 1 wherein R is an iodooacetoxy group of the formula ICH$_2$C00- and of the structure:

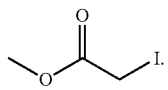

7. The compound of claim 1 wherein X is t-butyldimethylsilyl.

8. A pharmaceutical composition containing an effective amount of at least one compound as claimed in claim 1 together with a pharmaceutically acceptable excipient.

9. The pharmaceutical composition of claim 8 wherein said effective amount comprises from about 0.01 µg to about 1000 µg per gram of composition.

10. The pharmaceutical composition of claim 8 wherein said effective amount comprises from about 0.1 µg to about 500 µg per gram of composition.

11. 22-bromoacetoxy-homopregnacalciferol of the structure:

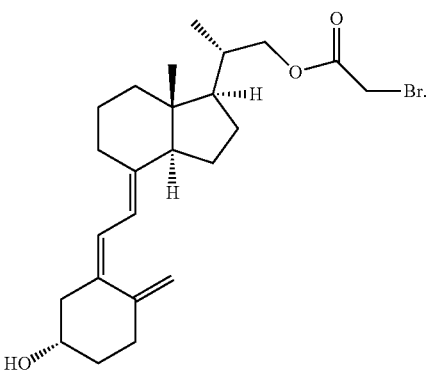 [SMILES: C=C1CC[C@H](O)C/C1=C/C=C1\CCC[C@]2(C)[C@@H]([C@H](C)COC(=O)CBr)CC[C@@H]12]

12. A pharmaceutical composition containing an effective amount of 22-bromoacetoxy-homopregnacalciferol together with a pharmaceutically acceptable excipient.

13. The pharmaceutical composition of claim 12 wherein said effective amount comprises from about 0.01 µg to about 1000 µg per gram of composition.

14. The pharmaceutical composition of claim 12 wherein said effective amount comprises from about 0.1 µg to about 500 µg per gram of composition.

15. 22-fluoroacetoxy-homopregnacalciferol of the structure:

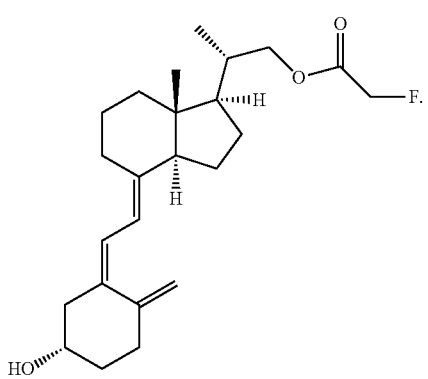 [SMILES: C=C1CC[C@H](O)C/C1=C/C=C1\CCC[C@]2(C)[C@@H]([C@H](C)COC(=O)CF)CC[C@@H]12]

16. A pharmaceutical composition containing an effective amount of 22-fluoroacetoxy-homopregnacalciferol together with a pharmaceutically acceptable excipient.

17. The pharmaceutical composition of claim 16 wherein said effective amount comprises from about 0.1 µg to about 1000 µg per gram of composition.

18. The pharmaceutical composition of claim 16 wherein said effective amount comprises from about 0.1 µg to about 500 µg per gram of composition.

19. 22-chloroacetoxy-homopregnacalciferol of the structure:

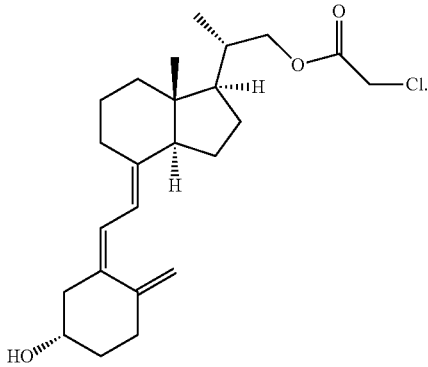 [SMILES: C=C1CC[C@H](O)C/C1=C/C=C1\CCC[C@]2(C)[C@@H]([C@H](C)COC(=O)CBr)CC[C@@H]12]

20. A pharmaceutical composition containing an effective amount of 22-chloroacetoxy-homopregnacalciferol together with a pharmaceutically acceptable excipient.

21. The pharmaceutical composition of claim 20 wherein said effective amount comprises from about 0.01 μg to about 1000 μg per gram of composition.

22. The pharmaceutical composition of claim 20 wherein said effective amount comprises from about 0.1 μg to about 500 μg per gram of composition.

23. 22-iodoacetoxy-homopregnacalciferol of the structure:

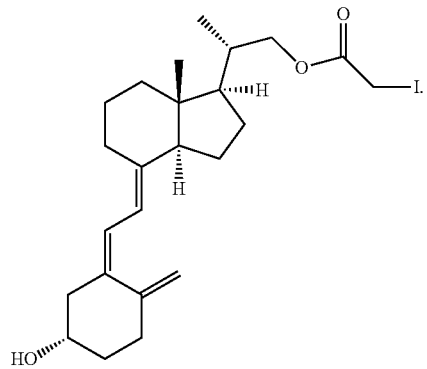 [SMILES: C=C1CC[C@H](O)C/C1=C/C=C1\CCC[C@]2(C)[C@@H]([C@H](C)COC(=O)CF)CC[C@@H]12]

24. A pharmaceutical composition containing an effective amount of 22-iodoacetoxy-homopregnacalciferol together with a pharmaceutically acceptable excipient.

25. The pharmaceutical composition of claim 24 wherein said effective amount comprises from about 0.1 μg to about 1000 μg per gram of composition.

26. The pharmaceutical composition of claim 24 wherein said effective amount comprises from about 0.1 μg to about 500 μg per gram of composition.

27. A method of treating a disease selected from the group consisting of leukemia and lung cancer comprising administering to a subject with said disease an effective amount of the compound of claim 1.

28. The method of claim 27 wherein the compound is administered orally.

29. The method of claim 27 wherein the compound is administered parenterally.

30. The method of claim 27 wherein the compound is administered transdermally.

31. The method of claim 27 wherein the compound is administered rectally.

32. The method of claim 27 wherein the compound is administered nasally.

33. The method of claim 27 wherein t compound is administered sublingually.

34. The method of claim 27 wherein the compound is administered in a dosage of from about 0.01 μg/day to about 1000 μg/day.

35. The method of claim 27 wherein R is a fluoroacetoxy group of the formula $FCH_2COO-$ and of the structure:

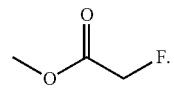

36. The method of claim 27 wherein R is a chloroacetoxy group of the formula $ClCH_2COO-$ and of the structure:

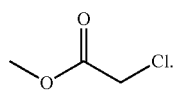

37. The method of claim 27 wherein R is a bromoacetoxy group of the formula $BrCH_2COO-$ and of the structure:

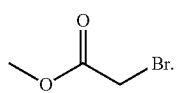

38. The method of claim 27 wherein R is an iodooacetoxy group of the formula $ICH-2COO-$ and of the structure:

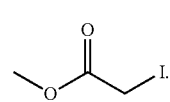

39. The method of claim 27 wherein the compound is 22-bromoacetoxy-homopregnacalciferol of the structure:

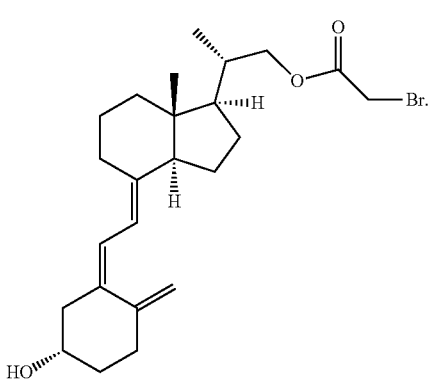

40. The method of claim 27 wherein the compound is 22-fluoroacetoxy-homopregnacalciferol of the structure:

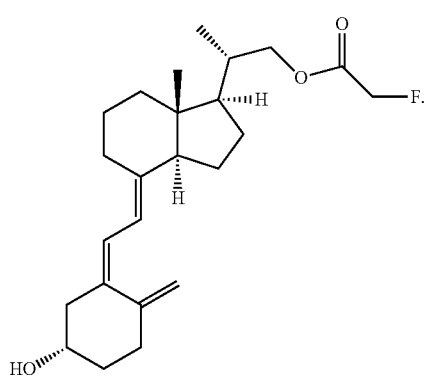

41. The method of claim 27 wherein the compound is 22-chloroacetoxy-homopregnacalciferol of the structure:

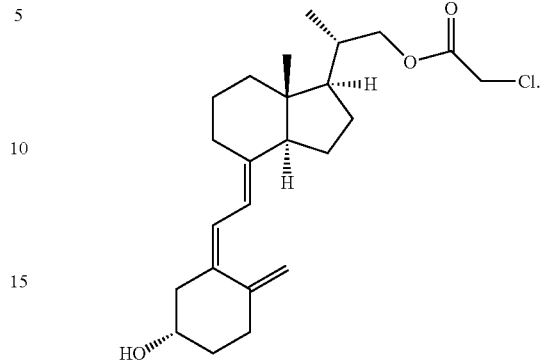

42. The method of claim 27 wherein the compound is 22-iodoacetoxy-homopregnacalciferol of the structure:

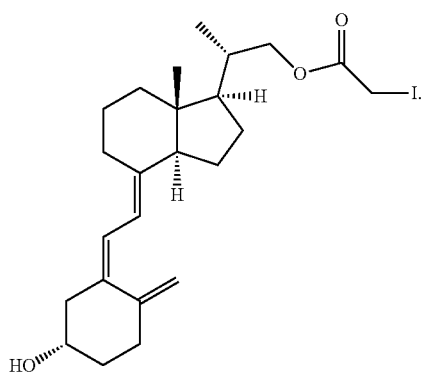

* * * * *